United States Patent [19]
O'Brien et al.

[11] Patent Number: 5,396,181
[45] Date of Patent: Mar. 7, 1995

[54] CARDIAC CATHETER TESTING APPARATUS

[76] Inventors: James O'Brien; James Heller, both of 1817 N. Cleveland, Chicago, Ill. 60614; Mark Houlton, 5251 Bolder Dr., Apt. D, West Des Moines, Iowa 50265

[21] Appl. No.: 16,880

[22] Filed: Feb. 11, 1993

[51] Int. Cl.⁶ .............................................. G01R 31/12
[52] U.S. Cl. ..................................... 324/556; 324/542
[58] Field of Search ............... 324/555, 556, 539, 542, 324/511; 604/21; 607/122, 27, 37; 128/642

[56] References Cited

U.S. PATENT DOCUMENTS

| | | | |
|---|---|---|---|
| 2,603,686 | 7/1952 | Lloyd | 324/555 |
| 2,839,723 | 6/1958 | Armond | 324/555 |
| 3,889,184 | 6/1975 | Bass | 324/510 |
| 4,114,091 | 9/1978 | Howard | 324/542 |
| 4,857,857 | 8/1989 | Valenti et al. | 324/555 |
| 4,866,390 | 9/1989 | Butchko | 324/556 |

FOREIGN PATENT DOCUMENTS 0256872 10/1988 Japan ................................. 324/555
0652506 3/1979 U.S.S.R. ............................ 324/542

Primary Examiner—Maura K. Regan
Attorney, Agent, or Firm—Welsh & Katz, Ltd.

[57] ABSTRACT

A cardiac catheter testing apparatus having a support structure including a plurality of receptacles adapted to removably receive a first probe of an electrical continuity measuring device. The support structure also includes electrical contact prongs adapted to removably receive the connective end of a cardiac catheter, which catheter has at least one electrode at the end of the catheter substantially opposite the connective end. The testing apparatus also includes electrical contact elements electrically connected to the receptacles to form an electrical path between the first probe when inserted in one of the receptacles, the electrical contact elements and the signal generating electrode. A second probe is electrically connected to the electrical continuity measuring device which displays a value indicating the presence or absence of electrical continuity between the electrode and the connective end of the catheter when the second probe is brought into contact with the electrode.

7 Claims, 1 Drawing Sheet

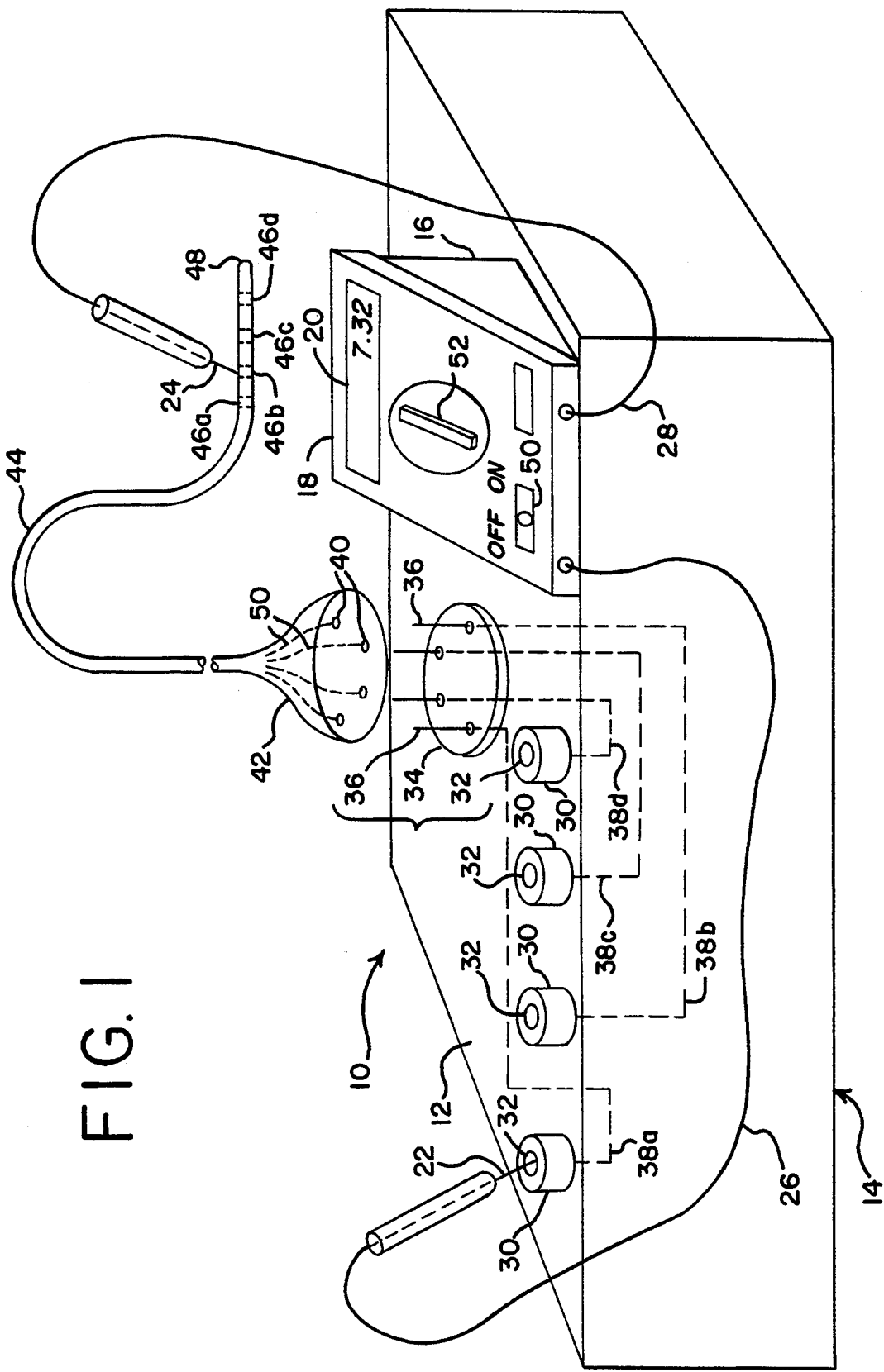

CARDIAC CATHETER TESTING APPARATUS

The present invention relates to an apparatus for readily determining the re-usability of non-lumen cardiac catheters, and more particularly to a novel testing structure for ease of measuring the continuity and reliability of the electrical path between the connective end and the electrode end of a non-lumen cardiac catheter.

BACKGROUND OF THE INVENTION

The use of single application, disposable medical devices is widespread among hospitals, clinics, and doctors' offices. This insures that each patient receives a workable, sterile device for each treatment, and the risk of spreading microbes between devices is eliminated. However, disposable medical devices are frequently very costly, thereby dramatically increasing the cost of medical treatments each time a new device is employed in a medical procedure.

It has been discovered that disposable medical products could be a key area for cost savings if changes in current practices and procedures relating to the use of disposable medical products could be effected. If devices initially designed for single application could be re-used, the price per use would fall, the overall cost of the particular procedure would drop, and if the volume of procedures in a medical facility remained constant, the cost would drop.

Cardiac catheters are one such class of disposable, single use devices which have been examined for possible re-usability. Common cardiac electrode catheters used in electrophysiologic treatment comprise a plurality of sensing or signal generating electrodes at one end of the catheter, with wires running internally through the length of the catheter and connected between each individual electrode at the opposite or connective end of the catheter. Some types of catheters used in such treatment include standard quadripolar catheters, bipolar catheters, tripolar catheters, and custom-made quadripolar catheters. The connective end of the catheter may comprise socket connecting elements individually attached to each of the wires leading from the electrodes. Alternately, the connective end of the catheter may comprise a plurality of wire ends leading from the catheter. In both situations, the socket elements or wires at the connective end of the catheter are adapted to be placed in electrical contact with a control device that transmits the electrical signals generated by the electrodes to a device for displaying the signal, such as a sinusoidal wave form, ultrasound image, numerical display, or the like. Cardiac catheters of the type mentioned above are usually non-lumen, woven Dacron®, multi-electrode pacing catheters.

Studies have shown that two primary considerations in the re-use of cardiac catheters are cleaning and sterilization to prevent the risk of spreading disease-bearing microbes, and the functional reliability of the catheter following repeated use. Sterilization just prior to re-use has been found to rid the catheter of microbes, whereupon when properly and rigorously cleaned, re-use of catheters did not create an obvious increase in the risk of infection. However, it has also been found that repeated sterilization may make the catheter and its electronic components fragile, thereby possibly leading to the deterioration of the mechanical and electrical properties of the catheter.

Currently, catheters to be re-used are subjected to several checks to determine their functional reliability. For example, a visual check is made to determine if any part of the catheter is cracked or too stiff to be used properly. This visual check will also reveal any outward physical damage to the tip or the electrodes of the catheter. Also, records are currently kept on the number of times a catheter has been re-used, and limits are placed on the maximum number of uses of a particular catheter.

As part of determining the functional reliability of the catheter prior to their sterilization and re-use, catheters presently are tested for electrical continuity, wherein a standard ohmmeter is used manually to measure resistance. This test requires a technician to hold one probe of the ohmmeter against a socket or wire at the connective end of the catheter, and the other probe against one of the electrodes at the electrode end of the catheter. The probe used at the electrode end of the catheter is serially brought into contact with each of the electrodes while holding the other probe in place against one of the sockets or wires at the connective end of the catheter. If there is continuity between the electrode and the socket or wire being contacted by the other probe, the ohmmeter will display the resistance value indicating electrical continuity in that wire. This test procedure is repeated for each wire in the catheter. The above described test procedure usually requires more than two hands to adequately hold the probes in place and to manipulate the probes properly, and becomes rather cumbersome to adequately complete. Also, when attempted manually, the probes may not make proper contact with the elements against which they are placed, possibly resulting in false positive or negative readings. A false negative reading may result in discarding a perfectly re-usable, and expensive, catheter. A false positive reading may result in inserting a defective catheter into the artery of a patient.

Therefore, an object of the present invention is to provide a testing apparatus for cardiac catheters which enables a technician to rapidly and accurately test the catheter for electrical continuity.

Another object of the present invention is to provide a testing apparatus for cardiac catheters which mechanically and positively maintains a connection between the connective end of the catheter and one of the probes of an electrical continuity testing device while a technician can readily manipulate the other probe of the testing device between the various electrode elements of the catheter.

A further object of the present invention is to provide a cardiac catheter testing apparatus having a support structure which maintains a probe of an electrical continuity testing device in electrical contact with one socket or wire formed in the connective end of the cardiac catheter, thereby enabling a technician to readily and accurately manipulate a second probe of the electrical continuity testing device against the electrodes at the electrode end of the cardiac catheter.

An additional object of the present invention is to provide a multi-electrode cardiac catheter testing apparatus having a support structure which forms an electrical contact path between each of the sockets or wires forming the connective end of the cardiac catheter and one of a plurality of receptacles. The receptacles are adapted to removably maintain a probe of an electrical continuity testing device in electrical contact with one of the sockets or wires of the cardiac catheter while another probe of the continuity testing device is manually brought into sequential contact with each of the multiple electrodes formed as part of the catheter.

SUMMARY OF THE INVENTION

These and other objects of the present invention are provided in a cardiac catheter testing apparatus including a support structure having receptacles adapted to removably receive a first probe of an electrical resistance measuring device, the support structure also including electrical contact elements adapted to removably receive the connective end of a cardiac catheter, where the catheter has at least one signal generating electrode at an end of the catheter substantially opposite the connective end of the catheter. Electrical contact elements are electrically connected to the receptacles to form an electrical path between the first probe inserted in one of the receptacles, the corresponding electrical contact element, and the signal generating electrode. A second probe is electrically connected to the electrical resistance measuring device, whereby the measuring device displays a value of electrical resistance when the second probe is brought into contact with one of the signal generating electrodes of the catheter.

BRIEF DESCRIPTION OF THE DRAWINGS

FIG. 1 is a perspective view of a cardiac catheter testing apparatus and a cardiac catheter, the testing apparatus constructed in accordance with the teachings of the present invention.

DESCRIPTION OF THE PREFERRED EMBODIMENT

Referring to FIG. 1, the cardiac catheter testing apparatus of the present invention is generally designated by the numeral 10, and includes a supporting base structure 12 and a hollow interior 14. Mounted on top of base 12 is a pedestal 16 which supports an electrical resistance measuring device 18, which could be an ohmmeter or any other similar electrical continuity testing apparatus. The measuring device 18 preferably has an alpha-numeric or numeric display 20 which provides a visible reading of electrical values, as will be described. First and second contact probes 22, 24 are connected by wires 26, 28, respectively to measuring device 18.

A plurality of receptacles 30 are mounted on top of base 12, and each receptacle includes a central aperture 32 extending to the base of each receptacle. The bottom of each aperture 32 comprises an electrically conductive material which is accessible to the hollow interior 14 of apparatus 10 through suitable holes formed in base 12 beneath each receptacle 30. The apertures 32 in receptacles 30 are sufficiently wide in diameter to receive probe 22 such that probe 22 makes electrical contact with the bottom of each receptacle 30. In addition, apertures 32 each have a width to depth configuration which maintains probe 22 in an upright position automatically.

A plate 34 is also mounted on base 12, and in the preferred embodiment of the invention, a plurality of electrically conductive prongs 36 extend upward from plate 34. The lower end of each prong 36 extends through suitable holes in base 12, and each prong 36 is connected to one of wires 38a, b, c or d. Wires 38a–d extend through hollow interior 14 to one of the electrically conductive materials at the base of each receptacle 30, thereby forming an electrical path between each of the prongs 36 to one of the receptacles 30.

Prongs 36 are configured on plate 34 to correspond to the configuration of sockets 40 of a plug 42 forming the connective end of catheter 44. Catheter 44 is preferably a luminless, woven Dacron ® multi-electrode pacing catheter of the type normally used in medical electrophysiologic processes. Such catheters include standard quadripolar catheters, catheters with bipolar electrodes, tripolar catheters, custom-made quadripolar catheters, or other similar electrode catheters. The catheter 44 includes a plurality of electrodes 46a, b, c and d, substantially at the end of the catheter opposite connective end 42, which end may be designated the electrode end 48. The catheter 44 includes a plurality of wires 50, each wire 50 extending internally of catheter 44 and connected at one end to one of the sockets 40 of plug 42, and at the other end to one of the electrodes 46a–d.

In FIG. 1, plug 42 forming the connective end of catheter 44 is shown in its disconnected position relative to plate 34 and prongs 36. To initiate operation of the cardiac catheter testing apparatus 10, plug 42 is inserted downward toward plate 34 so that each prong 36 is inserted in, and makes electrical contact with, a corresponding socket 40 in plug 42 of catheter 44. When this connection is made, a continuous electrical path is created between each of the signal generating electrodes 46a–d of catheter 44, along wires 50, sockets 40, prongs 36 and wires 38a–d, to each of the receptacles 30. In this manner, each of the electrodes 46a–d is electrically connected to a corresponding one of the receptacles 30 mounted on base 12.

To operate the cardiac catheter testing apparatus 10, the connective end 42 of catheter 44 is inserted over plate 34 and prongs 36 as described above. Resistance measuring device 18 is switched to its "on" position using switch 50. Dial 52 is positioned to display the appropriate and expected resistance value. First probe 22 is then placed in one of the receptacles 30 where the tip of first probe 22 makes electrical contact with the electrically conductive material at the bottom of the corresponding receptacle. Each receptacle 30 is sufficiently deep whereby first probe 22 is automatically maintained in an upright position in the corresponding receptacle, and is also held in electrical contact with the electrically conductive material at the bottom of the receptacle.

To test the electrical continuity between each signal generating electrode 46a–d and its corresponding socket 40 in connective end 42 of catheter 44, second probe 24 is next brought into contact with signal generating electrode 46a. However at this juncture of the test, the particular receptacle 30 into which first probe 22 is inserted may not be the receptacle in electrical contact with signal generating electrode 46a, and no reading may appear on display 20 of measuring device 18. Since a visual determination usually cannot be made as to the association between each electrode 46a–d and its corresponding socket 40 in plug 42, a mechanical-/electrical determination of this association can be made by sequentially placing second probe 24 into contact with the other signal generating electrodes 46b, c and d. When second probe 24 contacts the signal generating electrode which is electrically connected with first probe 22 and the receptacle 30 into which first probe 22 is inserted, a value will appear on display 20, indicating that electrical continuity still exists in that particular wire 50 in the catheter.

To continue the electrical continuity test of the remaining signal generating electrodes 46 of the catheter, first probe 22 is withdrawn from first receptacle 30, and is re-inserted into one of the other receptacles such that first probe 22 makes electrical contact with the base of the receptacle and is maintained in an upright position. Second probe 24 is then moved sequentially into contact with each of the other previously untested signal generating electrodes 46b-d until a value appears on display 20. This indicates that electrical continuity exists between the electrode in contact with second probe 24 and the socket 40 in plug 42 connected by a wire 50 to the particular signal generating electrode.

The above procedure is repeated by inserting first probe 22 in each of the remaining receptacles 30 and placing second probe 24 into contact with each of the remaining untested electrodes until values appear on display 20 indicating electrical continuity. However, upon testing some catheters 44, after first probe 22 has been inserted in one of the receptacles 30, it may occur that no value appears on display 20 upon placing second probe 24 in contact with each of the signal generating electrodes 46a-d. This is a positive indication that one of the signal generating electrodes 46a-d is not in electrical contact with its corresponding socket 40, although other electrodes may be in such contact with their corresponding sockets. If electrical continuity between any one of the signal generating electrodes and its corresponding socket in catheter 44 cannot be established using the above procedures, the catheter is defective and must be discarded. Likewise, if a value appears on display 20 of measuring device 18 for each of the signal generating electrodes 46a-d, electrical continuity exists between the connective end 42 of the catheter and each of the signal generating electrodes, and the catheter is re-usable.

After using cardiac catheter testing device 10 as described above to establish the re-usability of the catheter 44, the catheter is then thoroughly sterilized prior to use. Studies have shown that certain catheters can be re-used up to fifteen times if properly tested and sterilized. As part of a medical facility procedure for re-using catheters as described above, it is also important to maintain records showing how many times a catheter has been re-used. In this manner, a catheter will not be re-used beyond its outside limitations in view of operability and cleanliness.

The foregoing is considered as illustration only of the principles of the invention. Since numerous modifications and changes will readily occur to those skilled in the art, it is not desired to limit the invention to the exact construction and operation shown and described, and accordingly all suitable modifications and equivalents are deemed to fall within the scope of the following claims.

What is claimed:
1. A cardiac catheter testing apparatus comprising:
  a support structure including receptacle means for removably receiving a first probe of an electrical continuity measuring device;
  said support structure also including electrical contact means adapted to removably receive the connective end of a cardiac catheter, said catheter having at least one signal generating electrode at an end of said catheter substantially opposite said connective end, said at least one signal generating electrode being electrically connected to said connective end;
  said electrical contact means electrically connected to said receptacle means to form an electrical path between said first probe when inserted in said receptacle means, said electrical contact means and said signal generating electrode;
  second probe means electrically connected to said electrical continuity measuring device, said measuring device displaying a value indicating the presence or absence of electrical continuity between said electrode and said connective end of said catheter when said second probe is brought into contact with said signal generating electrode.

2. The cardiac catheter testing apparatus of claim 1 wherein said receptacle means includes an aperture extending through said receptacle means and electrical conductive means disposed in said aperture, said first probe making electrical contact with said electrical conductive means when said first probe is inserted in said aperture of said receptacle means.

3. The cardiac catheter testing apparatus of claim 1 wherein said receptacle means comprises a plurality of receptacles mounted on said apparatus, each of said receptacles including an aperture extending through said receptacle, electrical conductive means disposed at a lower end of each of said apertures, said first probe being automatically held in said receptacle in electrical contact with said electrical conductive means when said first probe is inserted in said aperture.

4. The cardiac catheter testing apparatus of claim 2 wherein said electrical contact means includes a plurality of prongs configured to correspond to a pattern of sockets forming the connective end of the catheter, said prongs being in electrical contact with a corresponding one of said electrical conductive means disposed in said apertures.

5. The cardiac catheter testing apparatus of claim 2 wherein said electrical conductive means is disposed at a lower end of said aperture.

6. A cardiac catheter testing apparatus comprising:
  an electrical continuity measuring device including a source of electrical current;
  a first probe having one end connected to the measuring device and a first contact element disposed on another end of said first probe;
  a second probe having one end connected to the measuring device and a second contact element disposed on another end of said second probe;
  said measuring device including electrical value display means,
  receptacle means mounted on a support structure, said receptacle means having aperture means therein for removably receiving and hold said first contact element of said first probe;
  said support structure also including connector means for removably receiving a connective end of a cardiac electrode catheter having a plurality of electrodes, said electrodes extending through said catheter,
  said connector means including a plurality of connector prongs, each of said prongs being electrically and separately connected to electrical conductive means disposed in said receptacle means,
  said second contact element of said second probe for contacting one of said plurality of electrodes of said cardiac catheter to determine electrical continuity between said one electrode, said measuring device, said aperture means, in contact with said first probe, one of the connector prongs of said connector means, and electrical path means extending between said connective end of said cardiac catheter device and said one electrode.

7. The cardiac catheter testing apparatus of claim 6 wherein said first contact element of said first probe is automatically held in said receptacle means when said first contact element is inserted in said receptacle means.

* * * * *